(12) United States Patent
Schoedinger, III et al.

(10) Patent No.: US 8,491,656 B2
(45) Date of Patent: Jul. 23, 2013

(54) ARTHRODESIS OF VERTEBRAL BODIES

(76) Inventors: George R. Schoedinger, III, St. Louis, MO (US); Albert N. Santilli, Pepper Pike, OH (US)

(*) Notice: Subject to any disclaimer, the term of this patent is extended or adjusted under 35 U.S.C. 154(b) by 1091 days.

(21) Appl. No.: 11/696,998

(22) Filed: Apr. 5, 2007

(65) Prior Publication Data

US 2008/0249626 A1  Oct. 9, 2008

(51) Int. Cl.
*A61F 2/44* (2006.01)

(52) U.S. Cl.
USPC .................................................. 623/17.16

(58) Field of Classification Search
USPC ............................................ 623/17.11–17.16
See application file for complete search history.

(56) References Cited

U.S. PATENT DOCUMENTS

| | | | |
|---|---|---|---|
| 4,743,256 A | 5/1988 | Brantigan | |
| 4,878,915 A | 11/1989 | Brantigan | |
| 5,669,909 A * | 9/1997 | Zdeblick et al. | 606/247 |
| 5,683,463 A * | 11/1997 | Godefroy et al. | 623/17.16 |
| 5,904,719 A * | 5/1999 | Errico et al. | 623/17.16 |
| 5,961,554 A | 10/1999 | Janson et al. | |
| 6,102,948 A | 8/2000 | Brosnahan, III | |
| 6,423,095 B1 * | 7/2002 | Van Hoeck et al. | 623/17.16 |
| 6,436,139 B1 * | 8/2002 | Shapiro et al. | 623/17.11 |
| 6,458,159 B1 | 10/2002 | Thalgott | |
| 6,471,725 B1 | 10/2002 | Ralph et al. | |
| 6,537,320 B1 | 3/2003 | Michelson | |
| 6,572,619 B2 | 6/2003 | Santilli | |
| 6,572,654 B1 * | 6/2003 | Santilli | 623/17.16 |
| 6,623,525 B2 | 9/2003 | Ralph et al. | |
| 6,660,038 B2 | 12/2003 | Boyer, III et al. | |
| 6,673,075 B2 | 1/2004 | Santilli | |
| 6,767,367 B1 | 7/2004 | Michelson | |
| 6,790,233 B2 | 9/2004 | Brodke et al. | |
| 6,881,228 B2 | 4/2005 | Zdeblick et al. | |
| 6,913,622 B2 | 7/2005 | Gjunter | |
| 6,923,830 B2 | 8/2005 | Michelson | |
| 6,981,975 B2 | 1/2006 | Michelson | |
| 7,056,342 B2 | 6/2006 | Michelson | |
| 7,112,206 B2 | 9/2006 | Michelson | |
| 2001/0011191 A1 * | 8/2001 | Kohrs | 623/17.16 |
| 2004/0204714 A1 * | 10/2004 | Liu et al. | 606/84 |
| 2004/0230305 A1 * | 11/2004 | Gorensek et al. | 623/17.11 |

OTHER PUBLICATIONS

John S. Collis, Cesar Rojas and Mark Janack, Anterior Total Disc Replacement: A Modified Anterior Lumbar Interbody Fusion, 1989, pp. 149-152, Aspen Publishing.

* cited by examiner

*Primary Examiner* — Sameh Boles
(74) *Attorney, Agent, or Firm* — Wayne D. Porter, Jr.

(57) ABSTRACT

Spinal arthrodesis is accomplished by implanting an intervertebral spacer made of a biocompatible material that promotes tissue ingrowth and bony fusion. The spacer is implanted into a graft bed formed between adjacent vertebral bodies. The spacer includes a body portion having anterior and posterior end faces. Opposed flanges project outwardly from the body portion at axial locations adjacent the anterior and posterior end faces. The flanges taper radially outwardly to an outer edge that is sharp enough to penetrate vertebral end plates. After a graft bed has been formed, and after the vertebral bodies have been distracted, the spacer is inserted into the graft bed and positioned such that the flanges are adjacent the vertebral end plates. Upon release of the distraction, the vertebral bodies will move toward each other and the flanges will be pressed into the end plates. The effect of the pressing action is to secure the spacer tightly in place within the graft bed such that migration of the spacer is prevented.

19 Claims, 4 Drawing Sheets

ARTHRODESIS OF VERTEBRAL BODIES

BACKGROUND OF THE INVENTION

1. Reference to Related Patents.

Reference is made to U.S. Pat. No. 5,961,554, issued Oct. 5, 1999 to Frank S. Janson and Albert N. Santilli; U.S. Pat. No. 6,572,619, issued Jun. 3, 2003 to Albert N. Santilli; U.S. Pat. No. 6,572,654, issued Jun. 3, 2003 to Albert N. Santilli; and U.S. Pat. No. 6,673,075, issued Jan. 6, 2004 to Albert N. Santilli (collectively "the Porous Spacer Patents"), the disclosures of which are incorporated herein by reference.

2. Field of the Invention.

The invention relates to the arthrodesis of vertebral bodies and, more particularly, to an intervertebral spacer that will not migrate within its graft bed, thereby promoting rapid arthrodesis.

3. Description of the Prior Art.

Techniques and devices for fusing two or more vertebrae of the spine together are well known. Such techniques commonly are performed to correct problems, such as chronic back pain, which result from degenerated intervertebral discs. One technique for fusing together two or more vertebrae of the lumbar spine involves performing a discectomy, i.e., excising all or a portion of the disc between adjacent vertebrae, and inserting one or more portions of an intervertebral spacer of a desired shape between the adjacent vertebrae. The intervertebral spacer may be inserted by either an anterior or posterior approach to the spinal column depending on a number of factors, including the number of vertebrae to be fused and past operative procedures. Upon healing, the vertebrae desirably are fused together through the intervertebral spacer. Such surgical fusion is known as arthrodesis.

Intervertebral spacers have been described by a number of names, including spinal implants and spinal cages. For convenience, all such devices will be referred to herein as "intervertebral spacers" or simply "spacers." There are a number of design features that must be taken into account in the construction of a suitable spacer. These features include the material from which the spacer is made, the external configuration of the spacer (and the mating graft bed in which the spacer will be implanted), and the extent and manner in which tissue ingrowth and bony fusion is permitted or promoted.

For many years, intervertebral spacers have been autogenic or autologous bone harvested from other areas of the body, such as the pelvis, allogenic bone taken from cadavers, or xenogenic bone, such as bovine bone sections. However, the use of substantially sized bone grafts can add complications to the fusion procedure. For example, when using an autologous bone graft, a second incision must be made in the patient to harvest the additional bone to be used in the graft, thus increasing the pain, blood loss, and trauma to the patient. When allogenic or xenogenic bone grafts are used there is a potential for the transmission of disease from the cadaver or other graft source to the patient.

More recently, non-biological spacers have been used, either alone or in combination with autologous, allogenic, or xenogenic fillers. A wide variety of materials have been used for these applications, but the best spacers have been made from metals that are bio-compatible with human tissue and that have desirable strength characteristics. Metals suitable for use as spacers include stainless steel as well as titanium, tantalum, niobium, and alloys and mixtures of these metals. Spacers made from these types of metals perform exceptionally well and, when properly sterilized, greatly minimize or eliminate the risk of infection or rejection.

As for the external configuration of the spacers, a variety of shapes, such as cylindrical or near-cylindrical, cubic, disc-like, and so forth has been employed. Reference is made to the Porous Spacer Patents for a disclosure of a number of shapes that can be employed for a spacer. Also, as shown in U.S. Pat. Nos. 4,878,915, 5,669,909 and 6,102,948, cylindrical and truncated conical spacers have been provided with threads along their length. These spacers can be threaded into a mating graft bed that is formed between adjacent vertebrae.

In considering whether a shape is suitable for a spacer, the difficulty in forming the graft bed must be taken into account. Generally, shapes are preferred that can be fitted into beds that can be prepared with minimal difficulty and with minimal removal of vertebral bone, provided that the shapes have adequate structural strength. Referring particularly to the cylindrical and truncated conical spacers referred to above, the graft bed usually is prepared by drilling. The bed can be tapped to receive the threads of the spacer, or the spacer can be forcibly threaded into the graft bed with the treads cutting their way through the end plates of the vertebrae or the remaining portions of the disc.

Another design consideration that must be taken into account is the extent to which tissue ingrowth and bony fusion is permitted or promoted. Some prior spacers have been provided in the form of bodies having pores or openings that permit bone ingrowth. Some of the openings are large enough to receive and hold bone or bone substitute. Since the object of the surgical procedure is to fuse the adjacent vertebrae, those spacers that promote bone ingrowth achieve a more rapid and stable arthrodesis.

Particularly effective non-biological spacers are disclosed in the Porous Spacer Patents. In these patents, spacers are made of a number of materials, including metal beads, metal wire mesh, or a combination of beads and wire mesh. Typically, the beads or wire mesh are made of a material such as titanium or titanium alloy. The spacers are made porous and strong by fusing the beads or wire mesh in a sintering operation that joins adjacent components at their points of contact. The spacers are completely porous throughout (on the order of 25 to 55 percent), which promotes desirable rapid tissue ingrowth and bony fusion. In addition to their inherent porosity, the spacers also can be provided with openings that can receive and hold bone or bone substitute.

In order to install the spacers disclosed in the Porous Spacer Patents, a graft bed is prepared in the spinal column by excising defective portions of a disc and portions of the adjacent vertebral bodies. If, for example, a cubic spacer is to be implanted, a cubic graft bed having approximately the same dimensions as that of the spacer would be prepared. Unfortunately, it is difficult and time-consuming to create a graft bed during the course of a surgical procedure that precisely conforms to the size and shape of a pre-existing spacer whose dimensions cannot be changed. Accordingly, it is possible for the spacer to fit relatively loosely in the graft bed. Such looseness may permit the spacer to change position, or migrate, while the healing process occurs. Since it takes about two months or more after implantation of a spacer for sufficient tissue ingrowth and bony fusion to occur, any post-operative migration of the spacer could extend the healing process or possibly render the spacer ineffective for its intended purpose.

The problem of migration also exists with respect to cylindrical or truncated conical spacers. Due to their threaded nature, such spacers can "back out" or otherwise become loosened in the graft bed after implantation. While the use of such spacers is desirable because it is relatively easy to form a graft bed by drilling, post-operative migration remains a problem.

Certain spacers have been proposed that include a plurality of radially projecting fins included as an integral part of a housing or as a movable assembly disposed within a housing. The housings typically are in the form of modified rectangular cubes that are placed in a graft bed. The housings or the movable assemblies can be rotated such that the fins cut into the vertebral end plates and thereby lock or attempt to lock the spacers in place. Such spacers are disclosed in the following U.S. Pat. Nos.: 6,537,320; 6,767,367; 6,923,830; 6,981,975; 7,056,342; and 7,112,206. While the referenced patents attempt to address the problem of spacer migration, it is believed that the shape of the spacers and the configuration of the fins are not an optimum approach to solving the problem.

In addition to post-operative migration, a number of difficulties still remain with many of the spacers currently available. While it is recognized that a hollow spacer containing bone or bone substitute disposed within the implant is a desirable technique for achieving fusion, some of the prior art devices have difficulty in achieving this fusion, at least without the aid of some additional stabilizing device, such a rod or plate. It has been found that the size of the openings in the spacer plays an important role in avoiding stress shielding of any bone implanted within the spacer. In other words, if the openings are too small or improperly configured, autologous bone will not experience the compression loading that typically is found to be necessary to ensure rapid and complete fusion. In this instance, the bone impacted within the spacer may resorb or evolve into simply fibrous tissue, rather than the desired bony fusion mass. On the other hand, the bone ingrowth openings must not be so large or extensive in number that the spacer does not have enough structural integrity to support the heavy load and bending moments that will be applied to it.

Desirably, a strong, bio-compatible intervertebral spacer would exist that could be fitted into an easily prepared graft bed. Any such spacer hopefully would be easy to install and would be tightly secured in place once installed so that any post-operative migration of the spacer, with consequent disruption of the arthrodesis process, would be prevented. Preferably, any such spacer would permit rapid tissue ingrowth and bony fusion while exhibiting excellent strength characteristics.

SUMMARY OF THE INVENTION

In response to the foregoing concerns, the present invention provides a new and improved technique for spinal arthrodesis involving a new intervertebral spacer and a method for its installation. The spacer according to the invention includes a body portion having anterior and posterior end faces. Flanges project from the body portion at axial locations adjacent the anterior end face and the posterior end face. The flanges taper to a sharp outer edge.

In the preferred embodiment, first and second channels are disposed on either side of the body portion. Also in the preferred embodiment, first and second side walls are disposed on either side of the body portion, each side wall being disposed circumferentially between the first and second channels. In this embodiment, the body portion is a cylinder from which material is removed (or not included) to form the channels and from which the flanges project at the ends. By virtue of the foregoing construction, the side walls, in cross-section, define a circular arc, as do the outer edges of the flanges when viewed from the end.

Desirably, one or more bores extend through the body portion. The bores are of a size and shape to receive bone or bone substitute and to permit the bone or bone substitute to experience compression loading in use. If desired, bone or bone substitute also can be placed in the spaces defined by the channels and the surrounding vertebral structure.

The spacer according to the present invention can be manufactured by a number of techniques. One technique is to make the spacer in a unitary construction, as by casting or machining, and then to provide a porous coating on certain desired surfaces. Other techniques are disclosed in the Porous Spacer Patents. As disclosed in these patents, biocompatible materials such as titanium metal beads of a suitable size are sintered together in a mold of a desired size and shape to provide a spacer having favorable porosity and strength characteristics.

The spacer according to the present invention is intended to be inserted into a graft bed formed in a patient's spine between vertically adjacent end plates of vertebral bodies. The graft bed is formed by performing a discectomy, followed by scraping of the end plates to form raw, bleeding bone, and creation of furrows in the end plates, preferably by a drilling operation.

After formation of the graft bed, the vertebral bodies are distracted. While the vertebral bodies are distracted, the spacer is inserted into the graft bed and positioned so that the flanges are adjacent the furrows in the end plates. Thereafter, upon releasing the distraction, the vertebral bodies will move toward each other and the flanges will be pressed into the furrowed portions of the end plates. The effect of such pressing action is to secure the spacer tightly in place within the graft bed such that migration of the spacer is prevented.

The foregoing and other features and advantages of the invention are fully described hereinafter. The accompanying drawings constitute a part of the specification and illustrate an exemplary embodiment of the invention.

DESCRIPTION OF THE PREFERRED EMBODIMENT

Figure 1:
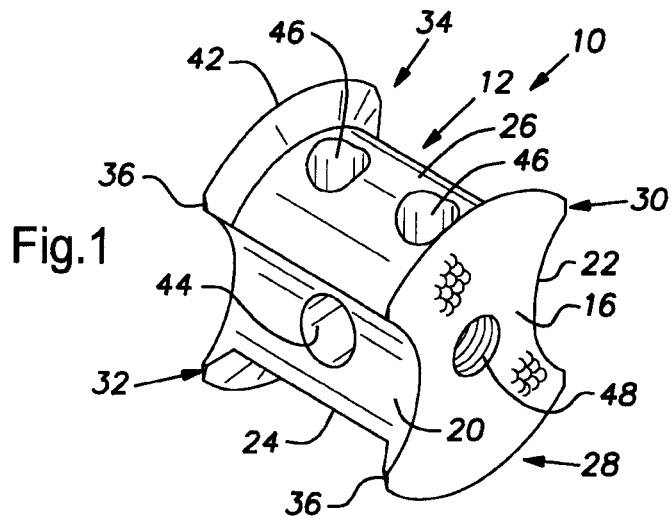
FIG. 1 is a perspective view of an intervertebral spacer in accordance with the present invention.
Figure 2:
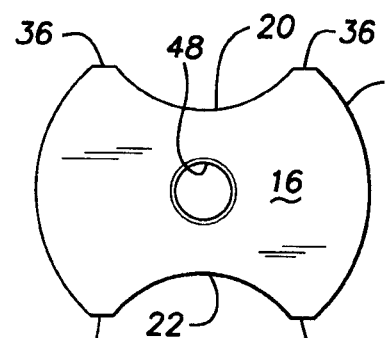
FIG. 2 is an end view of the spacer of FIG. 1.
Figure 4:
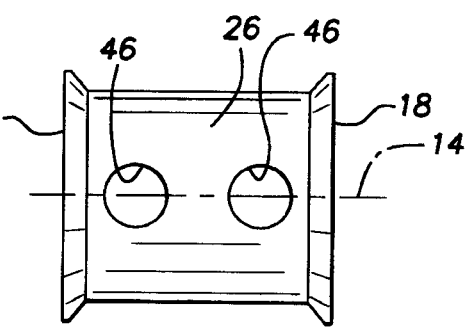
FIG. 4 is a view of the spacer of FIG. 1 viewed from the right in FIG. 3, with the spacer rotated 90 degrees.
Figure 3:
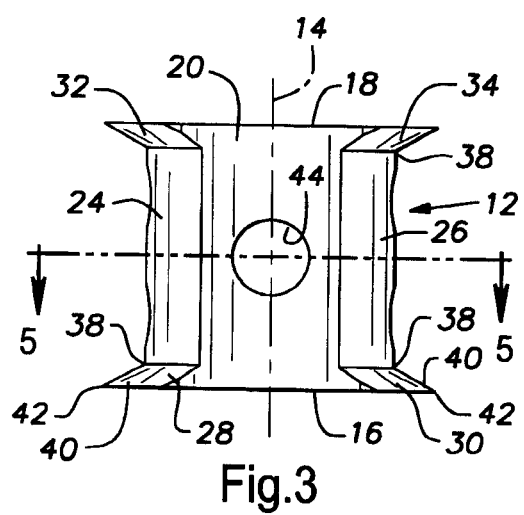
FIG. 3 is a side elevation view of the spacer of FIG. 1.
Figure 5:
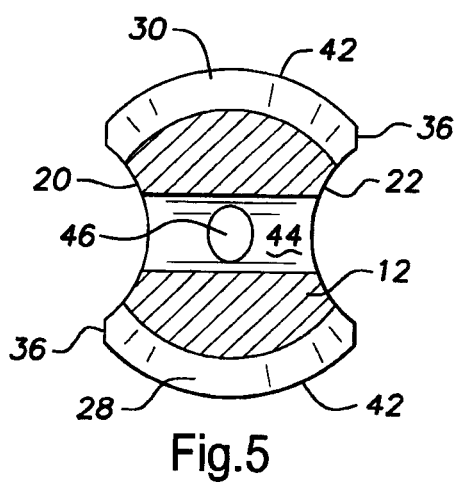
FIG. 5 is a cross-sectional view of the spacer of FIG. 1 taken along a plane indicated by line 5-5 in FIG. 3.

Referring to FIGS. 1-5, an intervertebral spacer in accordance with the present invention is indicated by the reference numeral 10. While the specific example of the intervertebral spacer 10 described herein is with reference to arthrodesis of vertebrae of the lumbar spine and the sacrum, the invention also applies to arthrodesis of vertebrae of the cervical and thoracic spine. Moreover, although the spacer 10 preferably is installed through an anterior approach to the spine, the spacer 10 also could be installed through a posterior approach to the spine, if desired.

The Spacer 10

The spacer 10 includes a body portion 12 having a longitudinal axis 14 and anterior and posterior end faces 16, 18, respectively. The spacer 10 is symmetrical about transverse and lateral planes taken through the center of the body portion 12. Thus, either of the faces 16, 18 could be denominated the anterior face or the posterior face. In the embodiment illustrated, the end faces 16, 18 are flat and are disposed generally, if not exactly, perpendicular to the axis 14. First and second opposed concave channels 20, 22 are disposed on either side of the body portion 12, the channels 20, 22 extending the length of the body portion 12 and opening through the end faces 16, 18. First and second opposed convex side walls 24, 26 are disposed on either side of the body portion 12. Each side wall 24, 26 is disposed circumferentially between the first and second channels 20, 22. The walls 24, 26 define the outer diameter of a cylinder whose centerline is the axis 14 and whose continuous surface is interrupted by the presence of the first and second channels 20, 22 (see FIGS. 1 and 5).

First and second flanges 28, 30 project radially outwardly from the anterior end face 16. The first and second flanges 28, 30 define the intersection between the first and second side walls 24, 26 and the anterior end face 16. Similarly, third and fourth flanges 32, 34 project radially outwardly from the posterior end face 18. The flanges 28, 30, 32, 34 have flat end portions 36 at each end thereof. The end portions 36 lie in a plane disposed generally perpendicular to the plane in which the anterior and posterior end faces 16, 18 lie. The flanges 28, 30, 32, 34, in cross-section, taper smoothly from a larger dimension 38 adjacent the first and second side walls 24, 26 to a smaller dimension 40 remote from the first and second side walls 24, 26. The smaller dimension 40 defines an edge 42 sufficiently sharp to cut into vertebral end plates. The edge 42, when viewed from the end, defines a circular arc drawn about the axis 14 (see FIGS. 2 and 5).

A first bore 44 extends through the body portion 12 and opens through the first and second channels 20, 22. A pair of second bores 46 extend through the body portion 12 and open through the first and second side walls 24, 26. As can be seen from an examination of FIGS. 1-5, the bore 44 and the bores 46 are disposed at right angles to each other. The bores 46 are disposed on either side of the bore 44. The bores 44, 46 are close enough to each other that they intersect each other in the region of the center of the body portion 12. In addition to the bores 44, 46, a threaded opening 48 is formed in the center of the posterior end face 18 concentric with the longitudinal axis 14. If desired, a threaded opening 48 can be formed in each of the end faces 16, 18. Alternatively, the threaded opening 48 can be in the form of an insert that is cast, welded, or otherwise secured in an opening in one or both of the end faces 16, 18.

The spacer 10 is sufficiently porous to facilitate tissue ingrowth and bony fusion, and preferably is made of a strong biocompatible material such as titanium, titanium alloys, cobalt-chromium alloys, tantalum, tantalum alloys, niobium, niobium alloys, stainless steel, and mixtures thereof. The spacer 10 can be made in a unitary manner such as by casting or machining. If a unitary construction is adopted, certain surfaces such as the side walls 24, 26 can be provided with a porous coating typically made of −45 +60 mesh. The spacer 10 also can be completely porous throughout, in which case the spacer 10 can comprise fused beads, fused strands of tortuous wire mesh, or a combination of fused beads and strands of tortuous wire mesh. It is expected that the spacer 10 will have 12-20 times the compressive strength of cortical bone.

Figure 11:
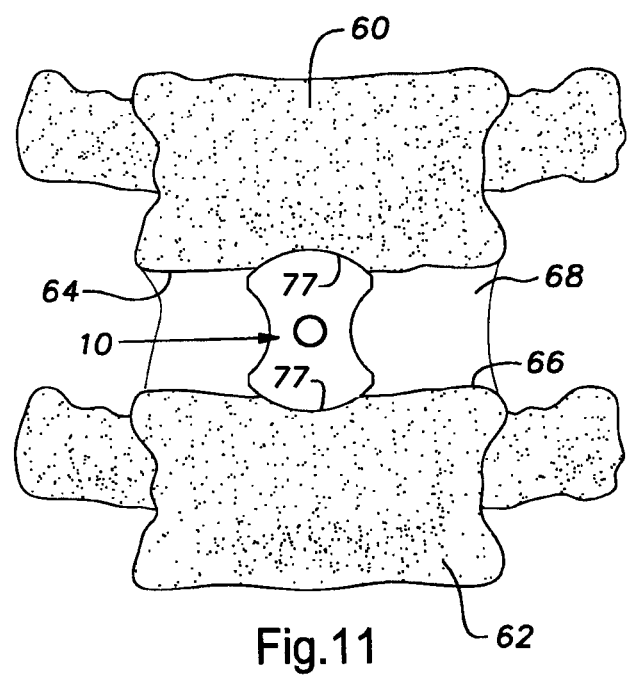
FIG. 11 is an anterior view similar to FIG. 6 showing a spacer according to the invention installed in a graft bed formed between two adjacent vertebrae.

The dimensions of the spacer 10 are such as will permit intervertebral bodies to be adequately spaced and ultimately fused together. Typically, a single spacer 10 will be used for vertebrae C1-C7, while two spacers 10 may be used for vertebrae L1-L5 (FIG. 11 shows only one spacer 10 being used). For use as a typical lumbar spacer, the distance between the end faces 16, 18 will be on the order of 20 mm, the radius of the channels 20, 22 will be about 9 mm from a point spaced about 15 mm from the axis 14, the radius of the side walls 24, 26 will be about 9.5 mm, and the radius of the edges 42 of the flanges 28, 30, 32, 34 will be about 12.5 mm measured from the axis 14. Those portions of the flanges 28, 30, 32, 34 that face each other are disposed at an angle of about 150 degrees from a line parallel with the axis 14.

The bores 44, 46 preferably are large enough to receive and properly compression load autologous bone or bone substitute while being small enough to preserve the structural integrity of the spacer 10. In the example illustrated, the bore 44 is about 6.35 mm in diameter, while the bores 46 are about 4.76 mm in diameter. The centerline of each bore 46 is spaced about 5.28 mm from the adjacent end face 16, 18. In addition to being able to place bone or bone substitute in the bores, 44, 46, the radius of the channels 20, 22 (about 9 mm in the example given) preferably is large enough to permit bone or bone substitute to be placed within the space defined by the channels 20, 22 and the surrounding vertebral structure after implantation of the spacer 10 has occurred. The threaded opening 48 is about 4.04 mm in diameter and extends to a depth of about 5 mm, with a 10-32 UNF threaded portion extending to a depth of about 4.02 mm.

As described more fully in the Porous Spacer Patents, the spacer 10 may be composed of biologically inert pellets that preferably are in the form of spherical beads. It will be appreciated that a variety of pellet shapes can be used, but a spherical shape is preferred. The pellets have a diameter such they occupy generally 45 to 75 percent of the volume of the spacer 10. The interstices between and among the pellets occupy generally 25 to 55 percent of the volume of the spacer 10. The foregoing proportions provide a spacer 10 that is sufficiently porous throughout to allow for the flow of bodily fluids through the spacer 10 and to promote tissue ingrowth and bony fusion with adjacent vertebrae. The pellets also result in porous surfaces over the spacer 10 which, when implanted, develop a high friction interface with the contacting vertebral bodies to facilitate maintaining the spacer 10 in place.

As disclosed in the Porous Spacer Patents, the pellets also can be made of titanium or a titanium alloy (such as Ti-6Al-4V) which is non-reactive within the body. Since the early 1970's, titanium and titanium alloys have been approved by the United States Food and Drug Administration for use in knee, shoulder, and hip implants to promote bone ingrowth. It also is possible to use other metals for the pellets, provided such metals are biocompatible. Such metals include cobalt-chromium alloys, tantalum, niobium, alloys of these metals, and possibly stainless steel.

The pellets also can be made of a plastics material such as PEEK (polyaryl, ether, ether ketone) resin which is believed to be non-reactive within the body. PEEK polymer is a high performance thermoplastic polymer made by Victrex plc of Westchester, Pa. PEEK polymer is semi-crystalline and is insoluble in all common solvents and has excellent resistance to a wide range of organic and inorganic liquids. The polymer retains excellent mechanical properties up to 572° F. It also can resist high dose levels of gamma radiation. It is an excellent choice for spinal implants and similar applications because it has a low value of coefficient of linear thermal expansion ($2.6 \times 10^{-5}$° F. by ASTM D696) up to the high glass transition temperature of 289° F. ($T_g$ by DSC).

It has been found that pellets of a certain size range are preferred. Suitable small pellets will have a mesh size of −45 +60 (0.009 inch to 0.011 inch). Suitable medium pellets will have a mesh size of −25 +30 (0.016 inch to 0.027 inch). Suitable large pellets will have a mesh size of −18 +30 (0.032 to 0.046 inch). The size of the pellets determines the porosity of the finished spacer 10. The larger the pellets, the greater the porosity. In certain applications, it may be desirable to mix pellets of various sizes to obtain a finished spacer 10 having a variable porosity.

The spacer 10 can be manufactured by a second technique. In the second technique, the spacer 10 is made of a plurality of fibers or strands that form a mesh. Titanium mesh presently is used as a porous coating for knee, shoulder, and hip implants. Such mesh sometimes is referred to a spaghetti mesh, and is commercially available from the Zimmer Company of Warsaw, Ind. Reference is made to U.S. Pat. Nos. 3,906,550; 4,693,721; and 5,665,119, the disclosures of which are incorporated herein by reference, for a discussion of the use of metal fiber as a porous bone structure material.

The spacer 10 can be manufactured by a third technique. In the third technique, the spacer 10 is made of a mixture of strands and pellets. If desired, the strands and the pellets could be made of metals such as titanium, titanium alloy, or a strong, non-reactive polymer such as PEEK. This spacer 10 has variable qualities of strength and porosity. In general, the use of a mixture of strands and pellets results in a stronger, less porous spacer 10.

In order to maintain the structural integrity of each embodiment of the spacer 10, the pellets, the strands, or the combination of pellets and strands must be fused together. One method of fusing PEEK pellets to form the spacer 10 includes placing the pellets into a cavity within a mold (not shown). The mold preferably is a three-piece mold forming a cavity of the finished dimensions of the spacer 10. The mold containing the PEEK pellets then is heated to a temperature high enough to cause sintering to occur. Other methods for fusing PEEK pellets or strands which provide a sufficiently strong spacer 10 also may be acceptable. When PEEK strands are used to form the spacer 10, the strands are placed in the mold in a tangled, tortuous mass. Sintering produces strong inter-strand bonds with variably sized openings to form a spacer 10 of suitable strength and porosity.

When sintering titanium or titanium alloy strands or pellets to form the spacer 10, the mold preferably is a substantially purified graphite mold. The mold is heated to a high temperature, for example, 2000 degrees F. or higher, until the sintering is complete, around 24 hours. Other conventional methods for fusing titanium which provide a sufficiently strong spacer 10 also may be acceptable. When titanium spaghetti mesh is used to form the spacer 10, the strands are placed in the mold in a tangled, tortuous mass. Sintering produces strong inter-strand bonds with variably sized openings to form a spacer 10 of suitable strength and porosity.

The spacer 10 can be manufactured by a fourth technique. In this technique, the spacer 10 is made of so-called foam metal that contains a plurality of interconnected voids. Foam metal, produced by mixing a powdered foaming agent with a metal powder, is a porous metal matrix with unique properties. One technique for forming foam metal is commonly known as "free-foaming." During free-foaming, a billet of metal containing a foaming agent is placed in a furnace and is heated to temperatures greater than the matrix metal. As the billet melts, the foaming agent releases gas in a controlled way. The gas discharge slowly expands the metal as a semi-solid foamy mass. The foaming process stops as the metal cools. Density is controlled by changing the foaming agent content and varying the heating conditions. U.S. Pat. No. 5,151,246, the disclosure of which is incorporated herein by reference, discloses a suitable technique for the manufacture of foam metal that could be used to produce the spacer 10 of the present invention.

Another technique for forming form metal is to mix a small quantity of powdered foaming agent with conventional metal powders to form a billet. The billet is heated by induction coils to a foaming temperature. The now-liquid billet is injected in a foaming state into complex molds. The injection of molten foam provides a versatile way to produce complex shapes of foam metal and can be utilized to produce a spacer 10 with non-uniform geometries.

The spacer 10 can be manufactured by yet another technique. In this technique, the spacer 10 is made of powdered metal that contains a plurality of interconnected voids. Powdered metal is produced by compressing and sintering various powdered metals. In conventional powdered metal technology, metal powder is compressed using accurately formed dies and punches in special types of hydraulic or mechanical presses. The compressed pieces then are sintered in an atmosphere-controlled furnace at high temperature to cause the metal particles to be bonded together metallurgically. A subsequent sizing or coining operation and a supplementary heat treatment may be employed. Powdered metals may be used to form irregularly curved or eccentrically shaped pieces.

The spacer 10 also can be made of powdered metal in a lost wax type of process. By this process, a mold is filled with a uniform mixture of wax beads, powdered metal and a low temperature binder. The mixture is compressed so that the mold is packed with the mixture. The mold then is heated to a first, relatively low, temperature to set the binder and melt the wax. Thereafter, the mixture is heated to a second, relatively high, sintering temperature to oxidize the binder and sinter the powder.

In accordance with a still further technique for making the spacer 10, the spacer 10 can be comprised of void-containing ceramic materials such as alumina or silica or combinations of ceramic materials. Reference is made to U.S. Pat. No. 6,039,762, the disclosure of which is incorporated herein by reference, for a description of suitable ceramic materials. The spacer can be formed as described previously, for example, by mixing ceramic powders with foaming agents and heating the mixture to a temperature adequate to form interconnected voids and sinter the ceramic ingredients.

Another technique for forming the spacer 10 is to take a solid block of a biologically inert, strong material such as PEEK polymer, titanium, or ceramic, the block being in a shape desired by the surgeon, and to drill or otherwise form a series of openings or bores in the block. Such openings or bores could be formed by EDM, chemical attack, or any other known machining technique such as mechanical drilling, laser drilling, water jet drilling, or plasma jet drilling. Preferably, the openings or bores are variably sized and variably spaced, and will intersect at numerous, randomly located places within the spacer so as to permit and promote tissue ingrowth and bony fusion.

Installation of the Spacer 10

The procedure for fusing two vertebrae together using the spacer 10 is substantially the same as the procedure for fusing vertebrae using a bone graft, but without many of the complications due to obtaining a suitable bone graft. The spacer 10 preferably is installed anteriorly. One anterior procedure for implanting a graft to fuse vertebra of the lumbar spine is discussed in Collis et al., "Anterior Total Disc Replacement: A Modified Anterior Lumbar Interbody Fusion," Lumbar Interbody Fusion, ed. Robert Watkins, Chapter 13, pp. 149-152, Aspen Publications (1989), the disclosure of which is incorporated herein by reference. Another anterior approach is disclosed in U.S. Pat. No. 5,669,909, the disclosure of which is incorporated herein by reference.

Figure 6:
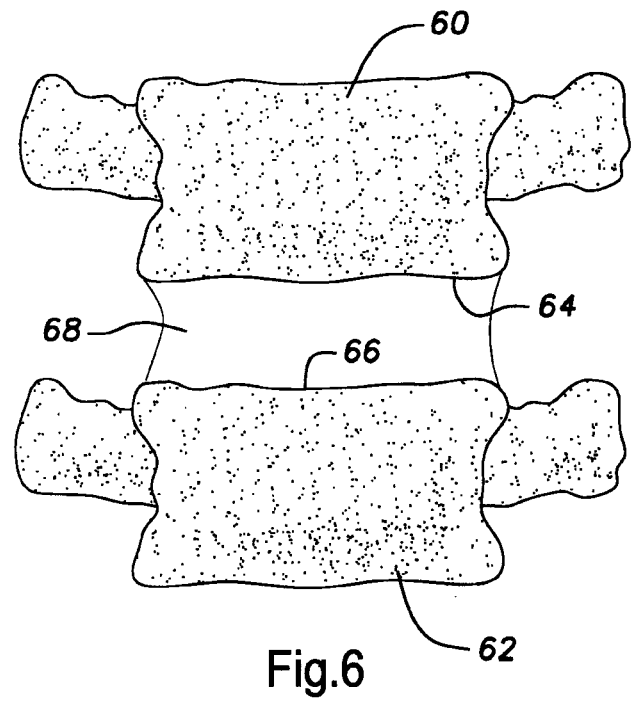
FIG. 6 is an anterior view of a portion of a patient's spine showing the L4 and L5 vertebrae.
Figure 7:
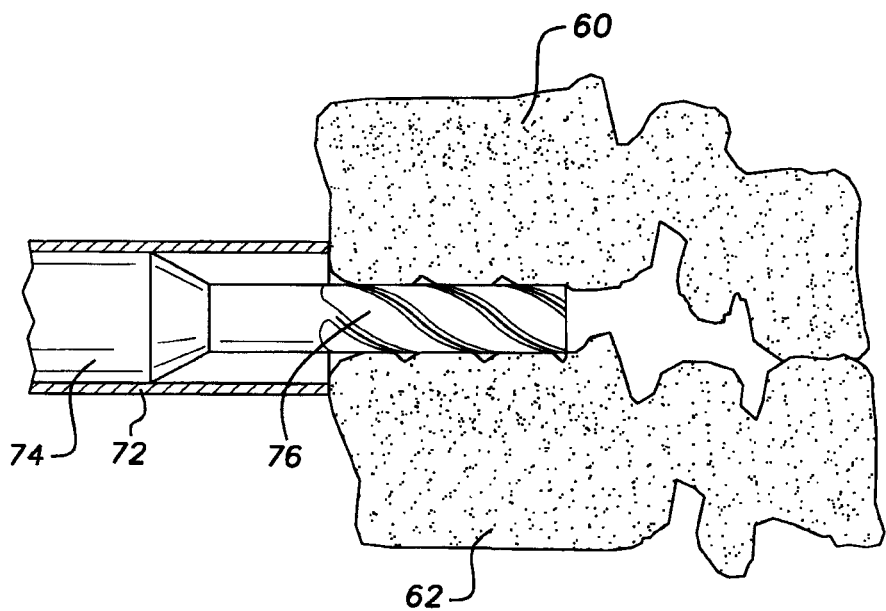
FIG. 7 is a view of the vertebrae of FIG. 6 taken along a sagittal plane showing a graft bed being formed by a drilling operation.

Referring now to FIG. 6, an anterior elevation view of the lumbar spine including the fourth (L4) and fifth (L5) lumbar vertebrae is shown. The L4 and L5 vertebrae are identified by reference numerals 60, 62. The vertebrae 60, 62 have end plates 64, 66, respectively, between which an intervertebral disc 68 is disposed. In FIG. 7, a graft bed 70 is prepared by surgically exposing the affected area and excising portions of the vertebral body of the vertebrae 60, 62 and the section of the disc 68 located therebetween. This is accomplished by inserting a trial plug (not shown) between the vertebrae 60, 62 in order to spread them a desired distance. Thereafter, a drill guide 72 is positioned firmly against the vertebrae. A reamer 74 having a bit 76 at one end is disposed within the drill guide 72. Upon rotating and pushing the reamer 74, the bit 76 will be advanced into the inter-vertebral space. This action of the bit 76 causes furrows 77 to be formed in the end plates 64, 66. The surfaces of the furrows 77 comprise raw, bleeding bone. The diameter of the bit 76 is selected such that the resultant furrows 77 are approximately the diameter of the side walls 24, 26.

Figure 8:
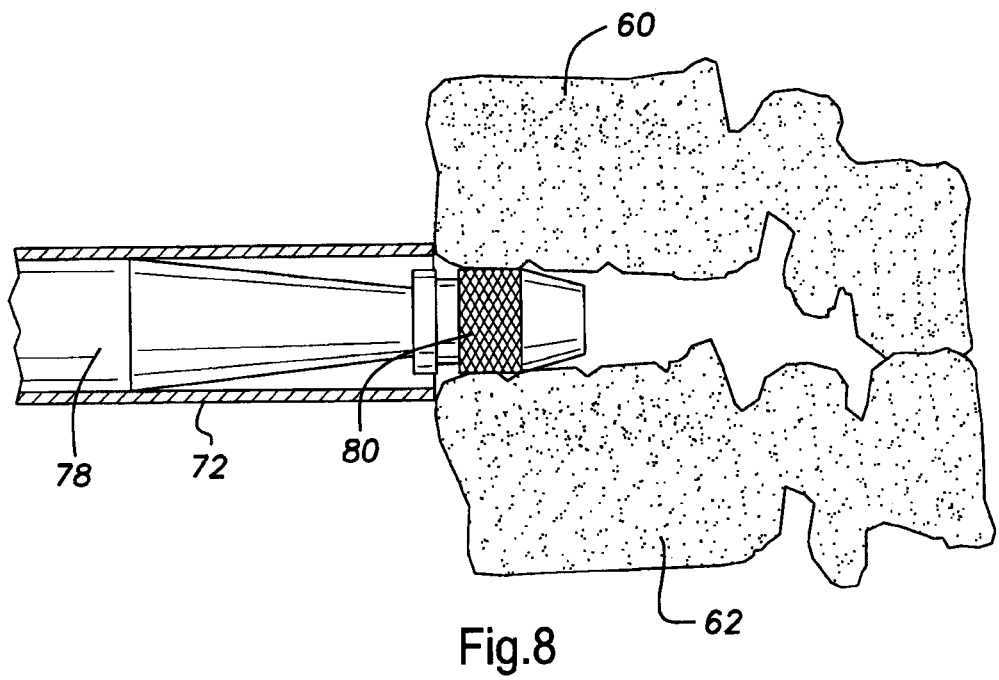
FIG. 8 is a view similar to FIG. 7 showing the vertebrae being distracted by a distraction tool.
Figure 9:
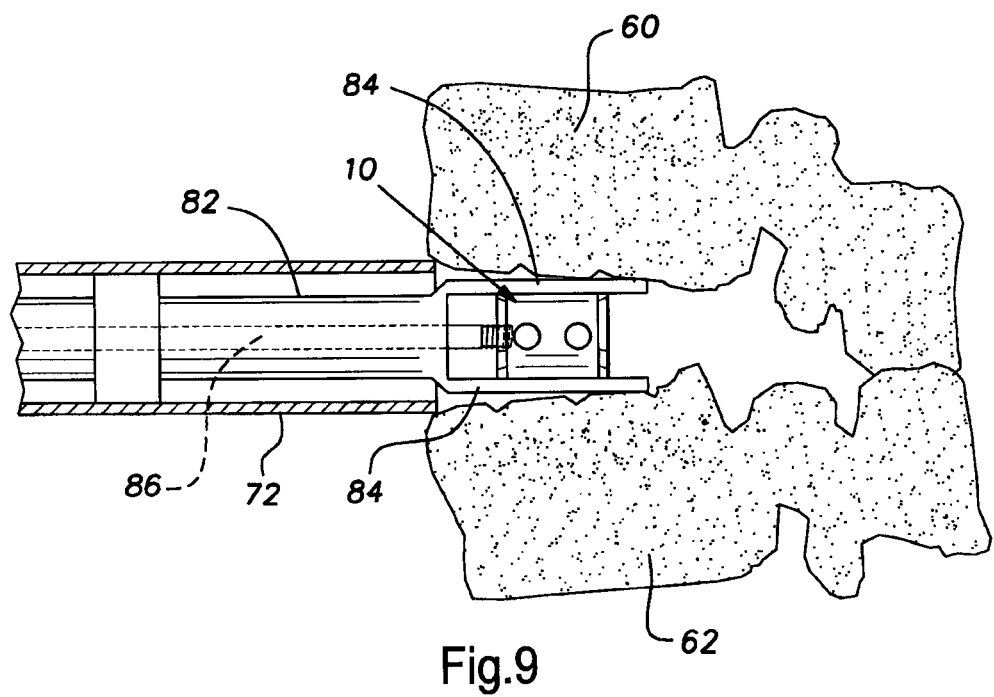
FIG. 9 is a view similar to FIG. 8 showing a spacer according to the invention moved into a preliminary position within the graft bed.

Referring now to FIG. 8, an obturator 78 having a plug 80 at one end is positioned within the drill guide 72. The plug 80 is pushed into the inter-vertebral space so as to distract the vertebrae 60, 62. As shown in FIG. 9, after distraction an insertion tool 82 having spaced fingers 84 at its end is positioned within the drill guide 72. The spacer 10 is securely held at the end of the tool 82 by means of a rotatable threaded rod 86 that engages the threaded opening 48. Any desired bone or bone substitute is placed within the bore 44 and/or the bores 46 prior to insertion of the spacer 10 within the drill guide 72. When the spacer 10 is held at the end of the drill guide 72, the fingers 84 are in contact with the opposing channels 20, 22. The spacer 10 is positioned so that the narrowest dimension is horizontal, i.e., the channels 20, 22 and the flat portions 36 are horizontally disposed. The presence of the flat portions 36 eliminates an otherwise sharp, pointed end of the flanges 28, 30, 32, 34, and slightly reduced the overall height of the spacer 10 so that it will fit readily into the graft bed 70.

Figure 10:
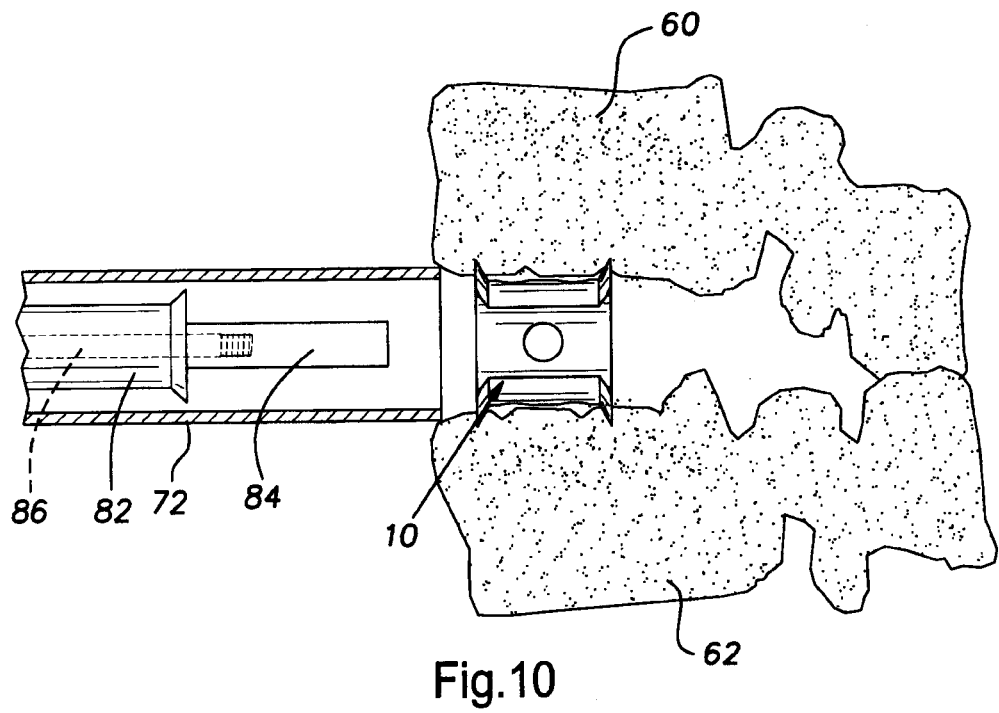
FIG. 10 is a view similar to FIG. 9 showing the spacer rotated into final position and the distraction of the vertebrae released.

Referring now to FIG. 10, after the spacer 10 has been inserted into the graft bed 70 a desired distance, the tool 82 is rotated 90 degrees. Rotation of the tool 82 causes the spacer 10 to be rotated about the axis 14 due to the interaction with the fingers 84. Rotation is continued until the flanges 28, 30, 32, 34 are positioned adjacent the opposing end plates 64, 66. Thereafter, the distraction is released, the rod 86 is unthreaded, and the tool 82 and the drill guide 72 are withdrawn. Release of the distraction causes the vertebrae 60, 62 to move toward each other such that the sharp-edged flanges 28, 30, 32, 34 are pressed into the end plates 64, 66. As a consequence of the flanges 28, 30, 32, 34 being pressed into the end plates 64, 66, the spacer 10 is secured tightly in place within the graft bed 70 such that post-operative migration of the spacer is prevented. At this point in the implantation process, any desired bone or bone substitute can be placed in the space defined by the channels 20, 22 and the surrounding vertebral structure.

As shown in FIG. 11, one spacer 10 can be installed between the vertebrae 60, 62. If desired, two or more spacers 10 may be used for vertebrae in the lumbar region. However, the number and placement of the spacers 10, as well as the specific dimensions of the spacers, are believed to be within the skill of the surgeon and further discussion here is unnecessary.

As will be appreciated from the foregoing description, an intervertebral spacer according to the invention is made of a biologically inert material that has enough strength to adequately support adjacent vertebral bodies and that is porous enough to permit tissue ingrowth and bony fusion. The spacer can be made from a variety of materials in a variety of manufacturing processes. Because the convex walls of the body portion preferably define a portion of a cylinder, the spacer can be rotated relatively easily for proper positioning in the graft bed, which itself preferably is cylindrical. Because the convex walls of the body portion and the edges of the flanges preferably conform to the shape of the graft bed, the stability of the spacer within the graft bed is enhanced. The use of only two flanges, one at each end of the spacer, causes the spacer to be secured in place without excessive cutting of the end plates. In all cases, the pressing action of the end plates of the vertebral bodies on the flanges of the spacer causes the spacer to be firmly held in place within the graft bed so that consequent disruption of the arthrodesis process is prevented.

Although the invention has been shown and described with respect to a certain preferred embodiment, various alterations and modifications may occur to others skilled in the art upon the reading and understanding of this specification. It is intended that the present invention include all such alterations and modifications and be limited only by the scope of the following claims.

What is claimed is:

1. An intervertebral spacer, comprising: a cylindrical body portion having a longitudinal axis and characterized by an absence of interior cavities along the longitudinal axis; anterior and posterior end faces; a porosity sufficient to facilitate tissue ingrowth and bony fusion, and a compressive strength greater than that of cortical bone; flanges projecting radially outwardly from the body portion at locations adjacent the anterior end face and the posterior end face, the flanges extending generally parallel with the anterior and posterior end faces and tapering radially outwardly to an outer edge sufficiently sharp to cut into vertebral end plates, the flanges, in cross-section, tapering from a larger dimension adjacent the first and second side walls to a smaller dimension remote from the first and second side walls; first and second channels disposed on either side of the body portion; first and second cylindrical, convex side walls disposed on either side of the body portion, each cylindrical, convex side wall being disposed circumferentially between the first and second channels, the cylindrical, convex side walls in use adapted to contact opposing vertebral bodies between which the intervertebral spacer is inserted; the flanges including first and second flanges defining the intersection between the first and second cylindrical, convex side walls and the anterior end face, the first and second flanges having end portions at each end thereof; the flanges including third and fourth flanges defining the intersection between the first and second cylindrical, convex side walls and the posterior end face, the third and fourth flanges having end portions at each end thereof; the flanges, when viewed from the end, defining an arc having a circumferential extent that approximates that of the first and second cylindrical, convex side walls; and wherein the first and second cylindrical, convex side walls are defined by an absence of protruding portions except for the flanges projecting radially outwardly from the body portion at locations adjacent the anterior end face and the posterior end face.

2. The intervertebral spacer of claim 1, wherein the first and second channels are concave.

3. The intervertebral spacer of claim 1, wherein the end portions of the flanges are flat.

4. The intervertebral spacer of claim 1, wherein the body portion includes bores formed therein, the bores being of a size and shape to receive bone or bone substitute and to cause the bone or bone substitute to experience compression loading in use.

5. The intervertebral spacer of claim 4, further comprising at least one bore extending through the body portion and opening through the first and second cylindrical, convex side walls and at least one bore extending through the body portion and opening through the first and second channels.

6. The intervertebral spacer of claim 1, wherein the end faces are flat and lie in planes that are generally perpendicular to the longitudinally extending axis.

7. The intervertebral spacer of claim 1, wherein a selected one of the anterior or posterior end faces includes a threaded opening, the threaded opening being concentric with the longitudinally extending axis.

8. The intervertebral spacer of claim 1, wherein the spacer is made of a construction selected from the group consisting of fused beads, fused strands of tortuous wire mesh, a combination of fused beads and strands of tortuous wire mesh, and a unitary structure having a porous coating on selected portions.

9. The intervertebral spacer of claim 1, wherein the spacer is made of a material selected from the group consisting of titanium, titanium alloys, cobalt-chromium alloys, tantalum, tantalum alloys, niobium, niobium alloys, stainless steel.

10. The intervertebral spacer of claim 1, wherein the body portion has a compressive strength 12-20 times greater than that of cortical bone.

11. An intervertebral spacer comprising: a cylindrical body portion having a longitudinal axis and characterized by an absence of interior cavities along the longitudinal axis; flat anterior and posterior end faces that are generally perpendicular to the longitudinal axis, the body portion having a porosity sufficient to facilitate tissue ingrowth and bony fusion and a compressive strength greater than that of cortical bone; first and second concave channels disposed on either side of the body portion, the channels extending the length of the body portion and opening through the end faces; first and second cylindrical, convex side walls disposed on either side of the body portion, each cylindrical, convex side wall being disposed circumferentially between the first and second channels, the cylindrical, convex side walls in use adapted to contact opposing vertebral bodies between which the intervertebral spacer is inserted; first and second flanges projecting radially outwardly from the anterior end face and extending generally parallel with the anterior end face, the first and second flanges defining the intersection between the first and second cylindrical, convex side walls and the anterior end face, the first and second flanges having flat end portions at each end thereof, the flanges, in cross-section, tapering smoothly from a larger dimension adjacent the first and second cylindrical, convex side walls to a smaller dimension remote from the first and second cylindrical, convex side walls, the smaller dimension defining an edge sufficiently sharp to cut into vertebral end plates, and the first and second flanges, when viewed from the end, defining an arc having a circumferential extent that approximates that of the first and second cylindrical, convex side walls; third and fourth flanges projecting radially outwardly from the posterior end face and extending generally parallel with the posterior end face, the third and fourth flanges defining the intersection between the first and second cylindrical, convex side walls and the posterior end face, the third and fourth flanges having flat end portions at each end thereof, the flanges, in cross-section, tapering smoothly from a larger dimension adjacent the first and second cylindrical, convex side walls to a smaller dimension remote from the first and second cylindrical, convex side walls, the smaller dimension defining an edge sufficiently sharp to cut into vertebral end plates, and the third and fourth flanges, when viewed form the end, defining an arc having a circumferential extent that approximates that of the first and second cylindrical, convex side walls; at least one first bore extending through the body portion and opening through the first and second channels; at least one second bore extending through the body portion and opening through the first and second cylindrical, convex side walls; and wherein the first and second cylindrical, convex side walls are defined by an absence of protruding portions except for the first and second flanges projecting radially outwardly from the anterior end face and the third and fourth flanges projecting radially outwardly from the posterior end face, respectively.

12. The intervertebral spacer of claim 11, wherein the spacer is made of a construction selected from the group consisting of fused beads, fused strands of tortuous wire mesh, a combination of fused beads and strands of tortuous wire mesh, and a unitary structure having a porous coating on selected portions.

13. The intervertebral spacer of claim 11, wherein the spacer is made of a material selected from the group consisting of titanium, titanium alloys, cobalt-chromium alloys, tantalum, tantalum alloys, niobium, niobium alloys, stainless steel.

14. The intervertebral spacer of claim 11, wherein a selected one of the anterior or posterior end faces includes a threaded opening, the threaded opening being concentric with the longitudinal axis.

15. The intervertebral spacer of claim 11, wherein the body portion has a compressive strength 12-20 times greater than that of cortical bone.

16. A method of creating arthrodesis in adjacent vertebrae of the spine, comprising the steps of: excising all or a portion of an intervertebral disc separating the adjacent vertebral bodies; distracting vertebral bodies that comprise the adjacent vertebrae; forming furrows of raw, bleeding bone in end plates of the vertebral bodies; providing an intervertebral spacer including a cylindrical body portion having a longitudinal axis and characterized by an absence of interior cavities along the longitudinal axis and having anterior and posterior end faces, the body portion having a porosity sufficient to facilitate tissue ingrowth and bony fusion and a compressive strength greater than that of cortical bone; flanges projecting radially outwardly from the body portion at locations adjacent the anterior end face and the posterior end face, the flanges extending generally parallel with the anterior and posterior end faces and tapering radially outwardly to an outer edge sufficiently sharp to cut into vertebral end plates, the flanges, in cross-section, tapering from a larger dimension adjacent the first and second side walls to a smaller dimension remote from the first and second side walls; first and second channels disposed on either side of the body portion; first and second cylindrical, convex side walls disposed on either side of the body portion, each cylindrical, convex side wall being disposed circumferentially between the first and second channels, the cylindrical, convex side walls in use adapted to contact opposing vertebral bodies between which the intervertebral spacer is inserted; the flanges including first and second flanges defining the intersection between the first and second cylindrical, convex side walls and the anterior end face, the first and second flanges having end portions at each end thereof;

the flanges including third and fourth flanges defining the intersection between the first and second cylindrical, convex side walls and the posterior end face, the third and fourth flanges having end portions at each end thereof; the flanges, when viewed from the end, defining an arc having a circumferential extent that approximates that of the first and second cylindrical, convex side walls; and wherein the first and second cylindrical, convex side walls are defined by an absence of protruding portions except for the flanges projecting radially outwardly from the body portion at locations adjacent the anterior end face and the posterior end face; and inserting the spacer into the graft bed while the vertebral bodies are distracted; disposing the flanges adjacent the furrows; and releasing the distraction such that the vertebral bodies move toward each other and the flanges are pressed into the end plates.

17. The method of claim 16, wherein the step of forming furrows in the end plates is accomplished by drilling.

18. The method of claim 17, wherein:
the first and second cylindrical, convex side walls have a diameter that approximates that of the furrows; and
the tapered flanges, when viewed from the end, define an arc that approximates that of the furrows.

19. The intervertebral spacer of claim 16, wherein the body portion has a compressive strength 12-20 times greater than that of cortical bone.

* * * * *